(12) United States Patent
Suzuki et al.

(10) Patent No.: US 10,591,400 B2
(45) Date of Patent: Mar. 17, 2020

(54) MICRO PARTICLE ANALYZER AND MICRO PARTICLE ANALYSIS METHOD

(71) Applicant: Sony Corporation, Tokyo (JP)

(72) Inventors: Yuya Suzuki, Kanagawa (JP); Fumitaka Otsuka, Kanagawa (JP); Masashi Kimoto, Tokyo (JP); Shingo Imanishi, Kanagawa (JP); Yoshitsugu Sakai, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 16/242,491

(22) Filed: Jan. 8, 2019

(65) Prior Publication Data

US 2019/0301994 A1    Oct. 3, 2019

Related U.S. Application Data

(60) Provisional application No. 62/650,081, filed on Mar. 29, 2018.

(51) Int. Cl.
*G01N 21/00* (2006.01)
*G01N 15/14* (2006.01)
*G01N 15/10* (2006.01)

(52) U.S. Cl.
CPC ..... *G01N 15/1425* (2013.01); *G01N 15/1404* (2013.01); *G01N 15/1434* (2013.01); *G01N 2015/1006* (2013.01); *G01N 2015/149* (2013.01); *G01N 2015/1481* (2013.01)

(58) Field of Classification Search
CPC ........... G01N 15/0205; G01N 15/1459; G01N 21/29; G01N 2015/1486; G01N 21/53
USPC ....................................................... 356/337
See application file for complete search history.

(56) References Cited

U.S. PATENT DOCUMENTS

| | | |
|---|---|---|
| 9,784,660 B2 | 10/2017 | Otsuka et al. |
| 9,857,286 B2 | 1/2018 | Muraki et al. |
| 9,915,935 B2 | 3/2018 | Muraki et al. |
| 10,180,676 B2 | 1/2019 | Muraki et al. |
| 10,241,025 B2 | 3/2019 | Otsuka et al. |
| 10,309,891 B2 | 6/2019 | Muraki et al. |

(Continued)

FOREIGN PATENT DOCUMENTS

WO    WO-2017068822 A1 *  4/2017  ......... G01N 15/1404

OTHER PUBLICATIONS

International Search Report and Written Opinion dated Jul. 26, 2019 in connection with International Application No. PCT/US2019/024803.

*Primary Examiner* — Md M Rahman
(74) *Attorney, Agent, or Firm* — Wolf, Greenfield & Sacks, P.C.

(57) ABSTRACT

The present technology provides a technology for stabilizing break-off timings. Therefore, according to the present technology, there is provided a microparticle analysis device or the like including at least: a flow path in which a fluid including a sample flow containing microparticles and a sheath flow flowing to contain the sample flow; a droplet formation unit configured to form a droplet in the fluid by imparting vibration to the fluid using a vibration element; an electric charge application unit configured to apply electric charge to a droplet containing the microparticles; an imaging unit configured to obtain a photo of a phase of a certain time; and a control unit configured to control a timing at which the droplet breaks off on a basis of the photo.

6 Claims, 10 Drawing Sheets

(56) References Cited

U.S. PATENT DOCUMENTS

| | | |
|---|---|---|
| 10,309,892 B2 | 6/2019 | Otsuka |
| 10,386,287 B2 | 8/2019 | Otsuka et al. |
| 2005/0112541 A1* | 5/2005 | Durack ............... C12N 5/0612 435/2 |
| 2005/0115313 A1* | 6/2005 | Luchsinger ........... G01F 1/6986 73/204.18 |
| 2011/0221892 A1 | 9/2011 | Neckels et al. |
| 2014/0261757 A1* | 9/2014 | Katsumoto ............... F17D 1/00 137/268 |
| 2015/0050638 A1 | 2/2015 | Marquette |
| 2015/0057787 A1 | 2/2015 | Muraki et al. |
| 2015/0068957 A1 | 3/2015 | Otsuka et al. |
| 2016/0245736 A1 | 8/2016 | Muraki et al. |
| 2016/0266027 A1 | 9/2016 | Muraki et al. |
| 2016/0327779 A1* | 11/2016 | Hillman ............... G02B 21/367 |
| 2017/0191925 A1 | 7/2017 | Otsuka et al. |
| 2017/0241889 A1 | 8/2017 | Otsuka et al. |
| 2018/0058999 A1 | 3/2018 | Otsuka et al. |
| 2018/0143609 A1 | 5/2018 | Muraki et al. |
| 2018/0313740 A1 | 11/2018 | Otsuka |
| 2019/0171179 A1 | 6/2019 | Muraki et al. |
| 2019/0219494 A1 | 7/2019 | Otsuka et al. |
| 2019/0271633 A1 | 9/2019 | Otsuka et al. |

* cited by examiner

MICRO PARTICLE ANALYZER AND MICRO PARTICLE ANALYSIS METHOD

CROSS REFERENCE TO RELATED APPLICATIONS

This Application claims priority under 35 U.S.C. § 119(e) to U.S. Provisional Application Ser. No. 62/650,081, entitled "MICRO PARTICLE ANALYZER AND MICRO PARTICLE ANALYSIS METHOD," filed on Mar. 29, 2018, which is herein incorporated by reference in its entirety.

TECHNICAL FIELD

The present technology relates to a microparticle analysis device and a microparticle analysis method.

BACKGROUND ART

A technology called flow cytometry is currently used for analysis of microparticles related to a field of living organisms such as cells and microorganisms. Flow cytometry is an analytical method of analyzing and sorting microparticles by radiating light to microparticles that flow to be contained in a sheath flow feeding a liquid in a flow path formed in a flow cell, a microchip, or the like and detecting fluorescence or scattered light emitted from the individual microparticles. A device used in such flow cytometry is called a flow cytometer (which may also be called a "cell sorter").

In such a flow cytometer, a vibration element is generally provided in a part of a flow path in which microparticles contained in a sheath flow flow. Vibration is imparted by this vibration element to a part of the flow path, and a fluid discharged from a discharge port of the flow path is continuously made into droplets. In addition, the flow cytometer employs a configuration in which predetermined electric charge is applied to a droplet containing microparticles, a traveling direction of the droplet is changed by a deflecting plate or the like on the basis of the electric charge, and only target microparticles are collected in a predetermined place or the like of a predetermined container or plate.

For a flow cytometer, a technique of controlling stable droplet formation is an important factor for improving accuracy in analysis. Here, it is known that, if formation of a droplet is unstable, such as when a break-off (break-off) timing at which a fluid discharged from a discharge port of a flow path is made into a droplet is unstable, or the like, a time at which an electric charge is applied to the droplet becomes unstable as well, and as a result, sorting of microparticles becomes unstable. However, control of the formation of a droplet is difficult because a plurality of factors such as environmental conditions such as flow rate, temperature, and humidity, sizes of microparticles, and the like are involved therein.

With regard to this matter, for example, Patent Literature 1 discloses a technology for stabilizing break-off timings. In this technology, a magnitude of vibration is controlled in accordance with a distance from a break-off point to a first satellite.

CITATION LIST

Patent Literature

Patent Literature 1: JP 2015-152439A

DISCLOSURE OF INVENTION

Technical Problem

However, further development of the technology of stable droplet formation has been desired.

Therefore, the present technology mainly aims to provide a technology for stabilizing break-off timings.

Solution to Problem

First, according to the present technology, there is provided a microparticle analysis device including at least: a flow path in which a fluid including a sample flow containing microparticles and a sheath flow flowing to contain the sample flow; a droplet formation unit configured to form a droplet in the fluid by imparting vibration to the fluid using a vibration element; an electric charge application unit configured to apply electric charge to a droplet containing the microp articles; an imaging unit configured to obtain a photo of a phase of a certain time; and a control unit configured to control a timing at which the droplet breaks off on a basis of the photo.

In the microparticle analysis device according to the present technology, the control unit may adjust a voltage of the vibration element on a basis of a timing at which the droplet specified in a plurality of the photos breaks off.

In addition, in the microparticle analysis device according to the present technology, the control unit may acquire a sequential photo of a phase of one period and specify a phase of a timing at which the droplet breaks off in the sequential photo. In this case, the control unit may acquire a sequential photo in which phases before and after the phase of the timing at which the droplet breaks off are further divided, and specify a phase of a timing at which the droplet breaks off in the divided sequential photo. In addition, in this case, the imaging unit may include a strobe, and the specification may be performed using a sequential phase photo obtained by changing a strobe light emission start time of the strobe.

In addition, in the microparticle analysis device according to the present technology, the control unit may perform control such that a phase of a timing at which the droplet breaks off becomes a phase corresponding to a back azimuth of a phase in which electric charge is applied to the droplet. In addition, the control unit may perform control such that a phase in which electric charge is applied to the microparticles comes between a phase in which a droplet before the droplet breaks off from a liquid column and a phase in which a satellite of the droplet breaks off from a liquid column.

In addition, according to the present technology, there is also provided a microparticle analysis method including at least: a droplet formation step of forming a droplet in a fluid including a sample flow containing microparticles and a sheath flow flowing to contain the sample flow by imparting vibration to the fluid using a vibration element; an electric charge application step of applying electric charge to a droplet containing the microparticles; an imaging step of obtaining a photo of a phase of a certain time; and a control step of controlling a timing at which the droplet breaks off on a basis of the photo.

In the control step of the microparticle analysis method according to the present technology, a voltage of the vibration element may be adjusted on a basis of a timing at which the droplet specified in a plurality of the photos breaks off.

In the present technology, "microparticle" can include a wide range of biological microparticles such as cells, microorganisms, and liposomes, synthetic particles such as latex particles, gel particles, and industrial particles, and the like.

Biological microparticles include chromosomes, liposomes, mitochondria, organelles (cell organelles) composing various cells, and the like. Cells include animal cells (e.g., hemocyte cells, etc.) and plant cells. Microorganisms include bacteria such as *Escherichia coli*, viruses such as tobacco mosaic virus, fungi such as yeast, and the like. Furthermore, biological microparticles also include biological polymers such as nucleic acids, proteins, complexes thereof, and the like. In addition, industrial particles may be of, for example, organic or inorganic polymeric materials, metals, and the like. Organic polymeric materials include polystyrene, styrene/divinylbenzene, polymethyl methacrylate, and the like. Inorganic polymeric materials include glass, silica, magnetic materials, and the like. Metals include gold colloid, aluminum, and the like. Although the shapes of these microparticles are normally spherical, non-spherical shapes may be possible, and a size, mass, and the like are not particularly limited in the present technology.

Advantageous Effects of Invention

According to the present technology, a technology of stabilizing break-off timings can be provided.

Note that effects described here are not necessarily limiting, and any effect described in the present disclosure may be admitted.

MODE(S) FOR CARRYING OUT THE INVENTION

Figure 1:
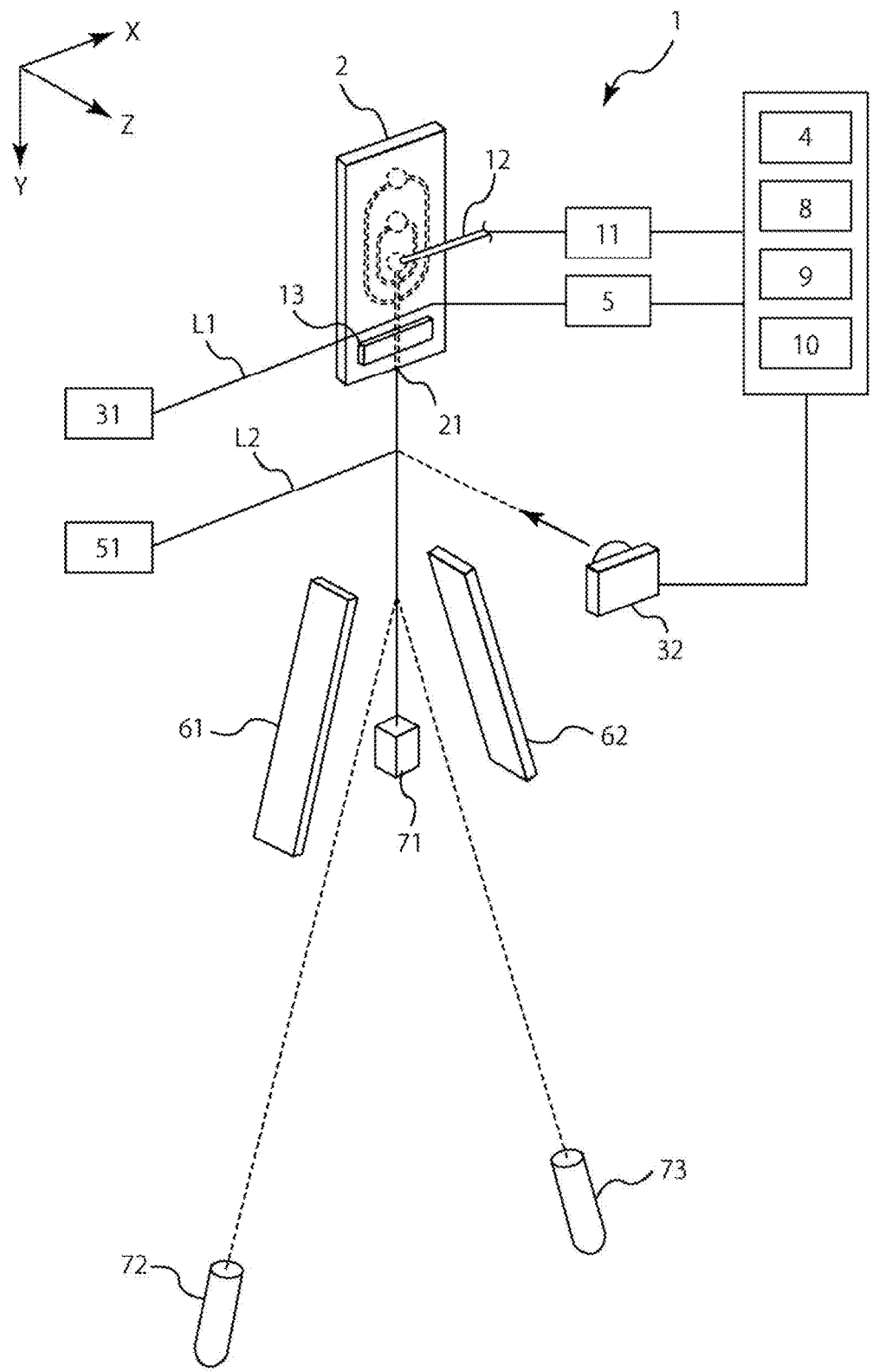
FIG. 1 is a schematic diagram illustrating an example of an embodiment of a microparticle analysis device 1 according to the present technology.

Preferred embodiments for implementing the present technology will be described below with reference to the drawings.

The embodiments described below show examples of a representative embodiment of the present technology, and the scope of the present technology is not narrowly interpreted thereby. Note that description will be provided in the following order.
1. Microparticle Analysis Device 1
(1) Flow path
(1-1) Microchip 2
(2) Droplet formation unit
(3) Electric charge application unit 11
(4) Imaging unit 3
(5) Control unit 4
[Control example 1]
[Control example 2]
[Control example 3]
[Control example 4]
(6) Detection unit 5
(7) Deflecting plates 61 and 62
(8) Collection containers 71 to 73
(9) Analysis unit 8
(10) Storage unit 9
(11) Display unit 10
(12) Input unit
(13) Others
2. Microparticle Analysis Method
(1) Droplet formation step
(2) Electric charge application step
(3) Imaging step
(4) Control step
[Example of Flow of Microparticle Analysis]
1. Microparticle Analysis Device 1

FIG. 1 is a schematic diagram illustrating an example of an embodiment of a microparticle analysis device 1 according to the present technology. The microparticle analysis device 1 (flow cytometer) according to the present technology includes at least a flow path, a droplet formation unit, an electric charge application unit 11, an imaging unit 3, and a control unit 4. In addition, the microparticle analysis device may also include a detection unit 5, deflecting plates 61 and 62, collection containers 71 to 73, an analysis unit 8, a storage unit 9, a display unit 10, an input unit, and the like if necessary. Each of the units will be described below in detail.

(1) Flow Path

In the flow path, a fluid composed of a sample flow including microparticles and a sheath flow flowing to contain the sample flow flows. This flow path may be provided in the microparticle analysis device 1 according to the present technology in advance, however, a disposable chip or the like in which a flow path is provided may be installed in the microparticle analysis device 1 to perform analysis or sorting.

A form of a flow path that can be used in the microparticle analysis device 1 according to the present technology is not particularly limited, and can be freely designed. In the present technology, it is particularly preferable to use a flow path formed within a substrate formed of a two-dimensional or three-dimensional plastic, glass, or the like.

In addition, a flow path width, a flow path depth, a flow path cross-sectional shape, and the like of the flow path are not particularly limited as long as they are in the form in which a laminar flow can be formed, and can be freely designed. For example, a micro-flow path having a flow path width of 1 mm or smaller can also be used in the micro analysis measurement device 1 according to the present technology. In particular, a micro-flow path having a flow path width of about 10 µm or greater and 1 mm or smaller is preferably used in the microparticle analysis device 10 according to the present technology.

(1-1) Microchip 2

Figure 2:
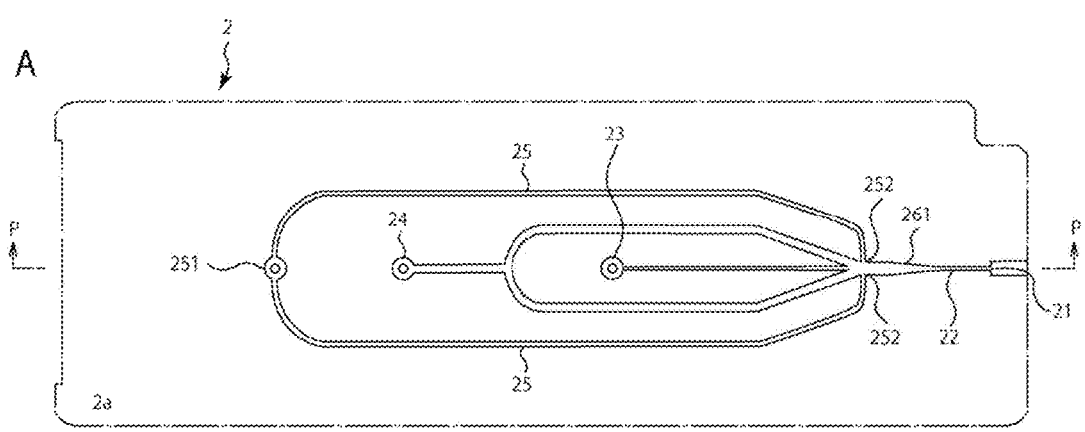
FIGS. 2 A and B are schematic diagrams illustrating an example of a configuration of a microchip 2 that can be used in the microparticle analysis device 1 of FIG. 1.
Figure 2:
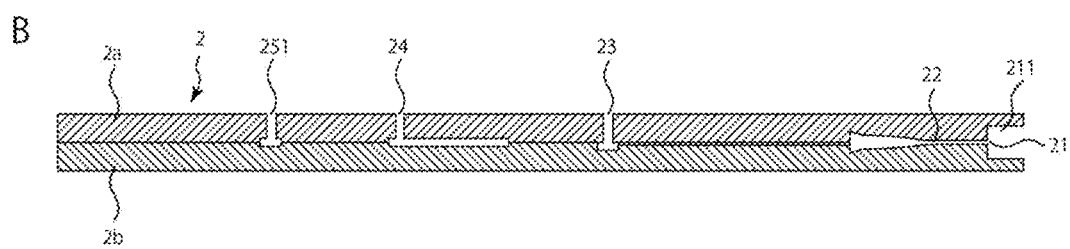
Figure 3:
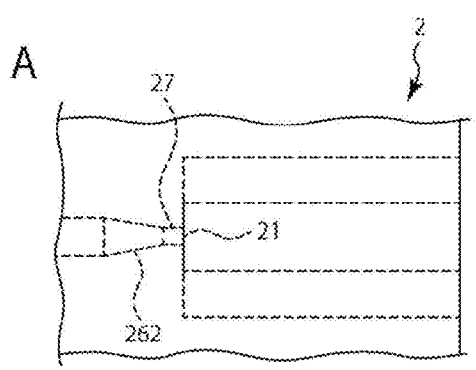
FIG. 3 A to C are schematic diagrams illustrating an example of a configuration of an orifice 21 of the microchip 2 that can be used in the microparticle analysis device 1 of FIG. 1.
Figure 3:
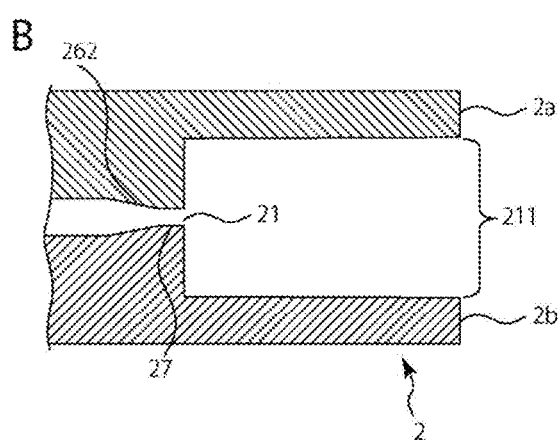
Figure 3:
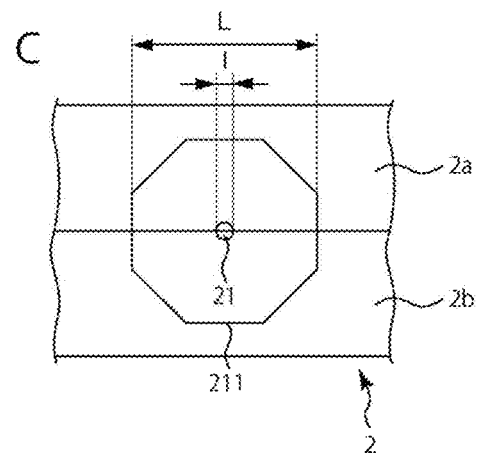

FIG. 2 shows schematic diagrams illustrating an example of a configuration of a microchip 2 that can be used in the microparticle analysis device 10 of FIG. 1, and FIG. 3 shows schematic diagrams illustrating an example of a configuration of an orifice 21 of the microchip 2 that can be used in the microparticle analysis device 1 of FIG. 1. A of FIG. 2 illustrates a schematic top view, and B of FIG. 2 illustrates a schematic cross-sectional view corresponding to a cross-section of the P-P line of A. In addition, A of FIG. 3 illustrates a top view, B of FIG. 3 illustrates a cross-sectional view, and C of FIG. 3 illustrates a front view. Note that B of FIG. 3 corresponds to a part of the cross-section of the P-P line of A of FIG. 2.

The microchip 2 is formed by laminating substrate layers 2a and 2b between which a sample flow path 22 is formed. The formation of the sample flow path 22 between the substrate layers 2a and 2b can be performed through injection molding of a thermoplastic resin using a mold. As the thermoplastic resin, a publicly-known plastic for a conventional microchip material such as polycarbonate, a polymethyl methacrylate (PMMA), a cyclic polyolefin, polyethylene, polystyrene, polypropylene, polydimethylsiloxane (PDMS), or the like can be employed.

In addition, in the microchip 2, a sample inlet 23 from which a sample containing microparticles from a liquid feeding contactor part is introduced, a sheath inlet 24 from which a sheath fluid is introduced, and the sample flow path 22 at which a sample flow is introduced and merges with the sheath fluid are formed. The sheath fluid introduced from the sheath inlet 24 is divided in two directions to be fed, and then merges with the sample fluid introduced from the sample inlet 23 at a junction with the sample fluid so that the sample fluid is sandwiched in two directions. Accordingly, a three-dimensional laminar flow in which a sample fluid laminar flow is positioned at the center of a sheath fluid laminar flow is formed at the junction.

25 shown in A of FIG. 2 represents a suction flow path for applying negative pressure into the sample flow path 22 to temporarily reverse the flow and thereby eliminate clogging and air bubbles when clogging or air bubbles occur in the sample flow path 22. At one end of the suction flow path 25, a suction outlet 251 connected to a negative pressure source such as a vacuum pump is formed. In addition, the other end of the suction flow path 25 is connected to the sample flow path 22 at a communication port 252.

A laminar flow width of the three-dimensional laminar flow narrows at narrowing parts 261 (see FIG. 2) and 262 (see A and B of FIG. 3) that are formed such that an area of a vertical section with respect to a liquid feeding direction decreases gradually or stepwise from upstream to downstream in the liquid feeding direction. Then, the three-dimensional laminar flow becomes a fluid stream and then is discharged from the orifice 21 provided at an end of the flow path. In FIG. 1, the discharge direction of the fluid stream from the orifice 21 is indicated by a Y axis positive direction.

A connection part of the sample flow path 22 to the orifice 21 is formed as a straight part 27 formed linearly. The straight part 27 functions to emit the fluid stream from the orifice 21 straight in the Y axis positive direction.

The fluid stream emitted from the orifice 21 is made into droplets by vibration applied to the orifice 21 by a vibration element 13, which will be described below, in accordance with a droplet frequency (droplet CLK). The orifice 21 is open in an end face direction of the substrate layers 2a and 2b, and a notch 211 is provided between the opening position and the end faces of the substrate layers. The notch 211 is formed by cutting the substrate layers 2a and 2b between the opening position of the orifice 21 and the substrate end faces so that a diameter L of the notch 211 is greater than an opening diameter l of the orifice 21 (see C of FIG. 3). It is preferable to form the diameter L of the notch 211 twice the size of the opening diameter l of the orifice 21 or more so that movement of droplets discharged from the orifice 21 is not obstructed.

(2) Droplet Formation Unit

The droplet formation unit forms droplets in the fluid by applying vibration to the fluid using the vibration element 13. It is preferable for the vibration element 13 to be provided to come in contact with the flow path, and more preferable that it be provided in the vicinity of a fluid discharge port of the flow path as illustrated in FIG. 1. Particularly, in a case in which the microchip 2 is used, it is preferable for the vibration element to be provided in the vicinity of the above-described orifice 21 of the microchip 2.

The vibration element 13 is not particularly limited, and a publicly-known element can be freely selected and used. Specifically, for example, a piezoelectric element or the like can be used. A liquid feeding amount with respect to the flow path, a diameter of the discharge port, and a frequency of the vibration element 13 or the like can be adjusted, a droplet size can be adjusted, and thereby droplets each containing a certain amount of microparticles can be generated.

(3) Electric Charge Application Unit 11

The electric charge application unit 11 applies positive or negative electric charge to a droplet containing microparticles. In the case in which the microchip 2 is used, electric charge is imparted to a droplet discharged from the orifice 21 formed in the microchip 2. The electric charge application unit 11 is disposed, for example, on an upstream side of the imaging unit 3, which will be described below, as illustrated in FIG. 1. The application of electric charge to a droplet is performed by an electrode 12 which is electrically connected to the electric charge application unit 11 and inserted into the sample inlet 23 provided in the microchip 2. Note that the electrode 12 may be inserted into any spot of the microchip 2 so that the electrode comes in electrical contact with the sample fluid or sheath fluid fed in the flow path.

In the microparticle analysis device 1 according to the present technology, after a drop delay time elapses from detection of microparticles contained in the sample fluid by the detection unit 5, which will be described below, the electric charge application unit 11 can apply electric charge to a droplet containing the microparticles.

(4) Imaging Unit 3

The imaging unit 3 obtains a photo of a phase (an image of a droplet) of a certain time. The reference numeral 31 in FIG. 1 is a droplet camera 32 such as a CCD camera or a CMOS sensor for imaging a droplet discharged from the orifice 21 of the microchip 2. The droplet camera 32 is disposed on a downstream side of the detection unit 5, which will be described below, and images at least a part of the fluid. In addition, the droplet camera 32 can adjust the focus of a captured droplet image. As a light source of the droplet camera 32 for performing imaging, for example, a strobe 31, which will be described below, is used. Note that, with the imaging unit 3, a plurality of photos can be obtained, and photos taken in a certain period can be sequentially acquired. "A certain period" mentioned here is not particularly limited, and it may be one period, which will be described below, or a plurality of periods. In the case of a plurality of periods, the periods may be continuous or discontinuous in terms of time.

An image captured by the droplet camera 32 can be displayed on the display unit such as a display, and can be used by a user to ascertain a situation of the droplet formation in the orifice 21 (e.g., a size, a shape, an interval, or the like of a droplet).

The strobe 31 may be controlled by the control unit 4, which will be described below. The strobe 31 is constituted by LEDs for imaging a droplet and a laser L2 (e.g., a red laser light source) for imaging microparticles, and light sources to be used are switched by the control unit 4 in accordance with an imaging purpose. A specific structure of the strobe 31 is not particularly limited, and one or two or more types of publicly-known circuits or elements can be freely selected and combined.

In a case in which LEDs are used for the strobe 31, the LEDs emit light only for a micro time in one droplet CLK period. The emission is performed at each droplet CLK, and accordingly, a certain moment of the droplet formation can be extracted as an image and acquired. Although a droplet CLK is about 10 kHz to 50 kHz while imaging using the droplet camera 32 is performed, for example, about 30 times per second, the present technology is not limited thereto.

In a case in which the laser L2 is used for the strobe 31, the laser L2 emits light in about half the period of the droplet CLK or a shorter period. In this case, since the laser L2 is caused to emit light after a light source lighting delay time set by the control unit 4 elapses only in a case in which the detection unit 5 detects microparticles, fluorescence of the microparticles contained in a droplet can be acquired from an image. By performing measurement under the condition that imaging by the droplet camera 32 is performed about 60 times per second, and detection of microparticles and light emission from the light source of the laser L2 are performed thousands of times per second, stable microparticles in which fluorescence of about dozens of microparticles is accumulated can acquire an image. Note that a light emission time of the laser L2 may be a time in which an image of stable microparticles can be acquired.

(5) Control Unit 4

The control unit 4 controls a timing at which a droplet breaks off on the basis of photos obtained by the imaging unit 3.

Here, a small droplet formed when a thin rod-like liquid column that has stretched to a backward side after discharge of the droplet is separated from a main droplet and a nozzle due to surface tension is called a "satellite" in the related art, and such a satellite is a cause of variable electric charge application to a droplet, and thus control of satellites has become an important parameter for a microparticle analysis device that needs to be accurate in a droplet deflection position.

Note that there are four types of satellites including a slow satellite (back satellite), infinity, a fast satellite (forward satellite), and a non-satellite. A slow satellite occurs when a lower end of the satellite is cut and then an upper end of the satellite is cut, infinity occurs when the lower end and the upper end of the satellite are cut at the same time, a fast satellite occurs when the upper end of the satellite is cut and then the lower end of the satellite is cut, and a non-satellite occurs when the upper end of the satellite is cut and the lower end of the satellite is absorbed before being cut.

A case in which a timing at which a satellite breaks off deviates from a timing at which electric charge is applied is one cause of occurrence of spatter. As shown in A of FIG. 4, in a state in which no spatter occurs, a target droplet is divided to the left and right because a certain amount of positive or negative electric charge is applied to the target droplet, and a non-target droplet passes through the center as it is because no electric charge is applied to the non-target droplet.

Figure 4:
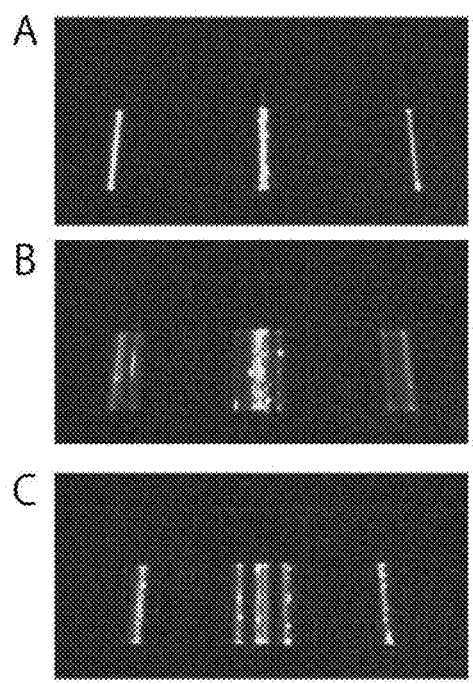
FIG. 4 A is a photo substituting for a diagram showing an appearance of a stream in a state in which no spatter occurs, and B and C thereof are photos, instead of diagrams, showing appearances of streams in a state in which spatter occurs.

However, when a deviation occurs in timings of application of electric charge, a state in which electric charge is properly applied to the target droplet and a state in which electric charge is not sufficiently applied (electric charge is not applied to a satellite) are mixed, and thus, as shown in B of FIG. 4, a plurality of streams are detected on the left and right sides. In addition, since there is a case in which electric charge is applied to a non-target droplet (electric charge is applied to a satellite), a plurality of streams are detected at the center as shown in C of FIG. 4.

Thus, if sorting is performed in the state in which spatter occurs, cells are not dropped at targeted positions, which causes a yield and a recovery rate to decrease. In addition, there is also a possibility of non-target microparticles being sorted out as well, which causes a decrease in purity.

Therefore, by the control unit 4 controlling a timing at which a droplet breaks off and preventing a deviation of a timing at which a satellite breaks off from a timing at which electric charge is applied using the present technology, stabilization in the break-off timing can be achieved.

In addition, indices such as a gap length (a distance from a break-off point to a satellite), a satellite length, and a droplet length were used in the past for the purpose of stabilizing break-off timings. That is, a portion other than a constricted part of a fluid immediately before the fluid is made into a droplet was observed, and a change in the constricted part was indirectly checked, and thereby control was performed. However, such indirect indices are likely to be easily affected by a difference in sizes of microparticles included in a sample fluid, a change in ambient temperature, and the like, and there is a possibility of performance not being maintained in a case in which a relation between the indices and the constriction collapses due to a disturbance. This is on the basis of the fact that, specifically, a force disturbing a surface works in accordance with vibration intensity due to coming microparticles having large sizes, which makes it easy to cause a shift in break-off, or a time to break-off mainly depends on a growth rate (a parameter related to vulnerability of a droplet to constriction), and if a change in fluid surface tension or a change in fluid density becomes linear and a physical amount such as a temperature fluctuates, it affects the state of the fluid, and thus the time to break-off changes.

However, in the present technology, it is possible to directly monitor a break-off point on the basis of photos obtained by the imaging unit 3, and thus performance can be improved against a significant temperature change as well as microparticles having large sizes.

Although a method of controlling a timing at which a droplet breaks off is not particularly limited, it is preferable to adjust a voltage of the vibration element 13 on the basis of a timing at which a droplet specified in a plurality of photos breaks off.

Control methods used by the control unit 3 will be described in more detail on the basis of the following control examples 1 to 4.

Control Example 1

Figure 5:
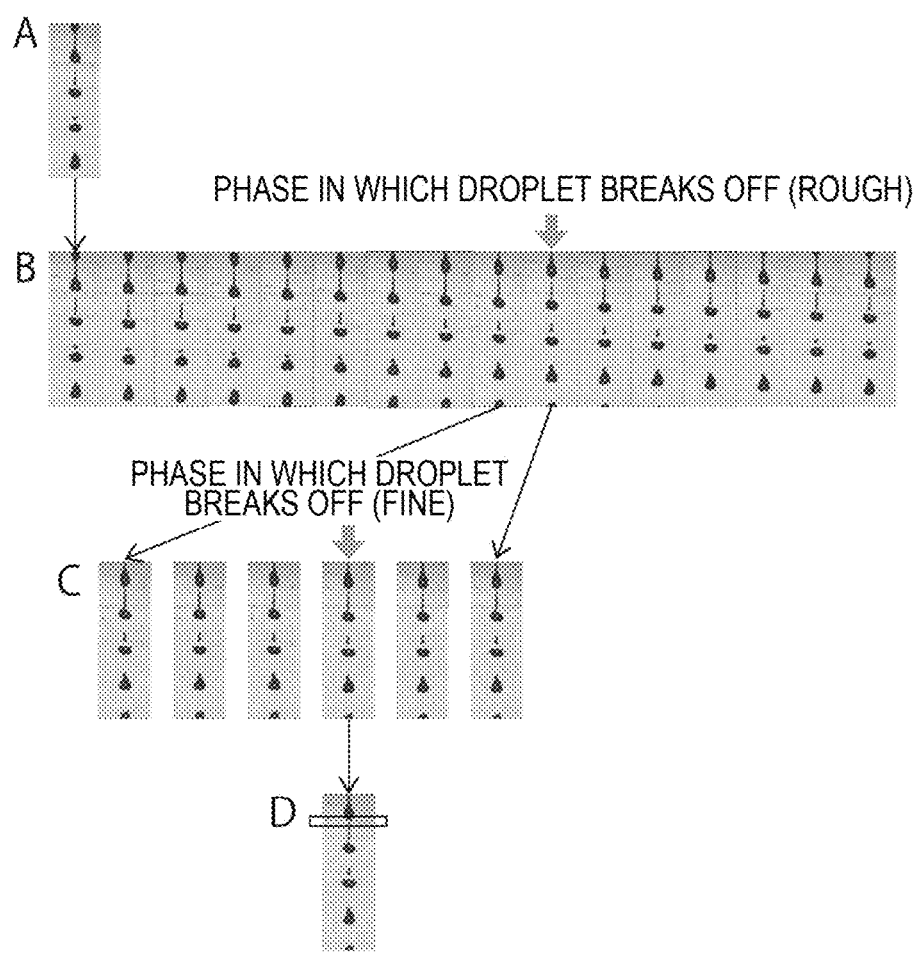
FIG. 5 A to D are diagrams illustrating a method of control example 1.

In the present control example 1, first, a droplet that does not spatter is created by automatically adjusting a droplet containing microparticles (see A of FIG. 5). Then, a sequential photo with phases in a certain period is acquired while shaking the strobe, and phases of a timing at which the droplet breaks off (a phase in which the droplet breaks off) are specified (see B of FIG. 5) in the sequential photo. Specifically, for example, a light emission period of the strobe is uniformly divided (e.g., into 16), and a phase in which the droplet breaks off is detected from images of the sequential photo of one period. Then, a sequential photo in which the phases before and after the aforementioned phase are further divided is acquired, and phases of a timing at which a droplet breaks off are more accurately specified in the divided sequential photos (see C of FIG. 5). Specifically, for example, the light emission period of the strobe is uniformly divided again (e.g., into 40), and phases in which a droplet breaks off are more accurately specified in images of sequential photos of one period.

Note that, in the present control example 1, a state in which a droplet breaks off also in the next phase to the phase in which the droplet breaks off may be ascertained before sequential photos in which the phases before and after the phase in which the droplet breaks off are further divided are acquired.

Figure 6:
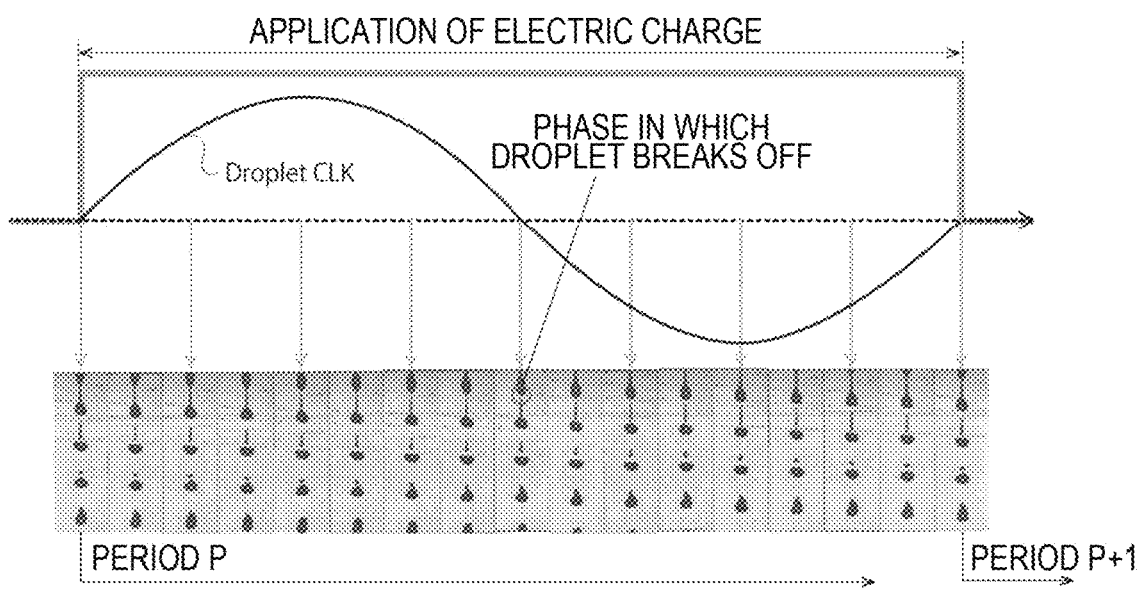
FIG. 6 is a photo substituting for a diagram showing a sequential photo in which one period is divided into 16.

FIG. 6 is a photo substituting for a diagram showing a sequential photo in which one period is divided into 16. This photo substituting for a diagram is a sequential phase photo obtained by changing a strobe light emission start time of the strobe provided in the imaging unit 3. The "one period" mentioned here means a time in which one droplet containing microparticles is formed, and is determined on the basis of a frequency of the vibration element 13 (e.g., a piezoelectric element). The frequency of the vibration element 13 is about 10 kHz to 50 kHz, and a time of one period is about $\frac{1}{10000}$ of a second at maximum and about $\frac{1}{50000}$ of a second at minimum.

In addition, the number of times a droplet breaks off and the number of times a droplet does not break off in a given time (e.g., 10 seconds) are investigated by monitoring break-off positions. Then, if the number of times of break-off exceeds a threshold value (e.g., 40 to 60%, or preferably 50%), the droplets tend to break off, and thus the voltage of the vibration element 13 is lowered to prevent the droplets from breaking off. On the other hand, if the number of times is smaller than the threshold value, the droplets tend to stick together, and thus the voltage of the vibration element 13 is increased to make it easy for the droplets to break off. That is, after images are acquired by dividing one period into uniform phases, the voltage of the vibration element 13 is adjusted so that the number of times of break-off in a specified phase in which break-off occurs is, for example, 40 to 60%, or preferably 50%.

Control Example 2

Figure 7:
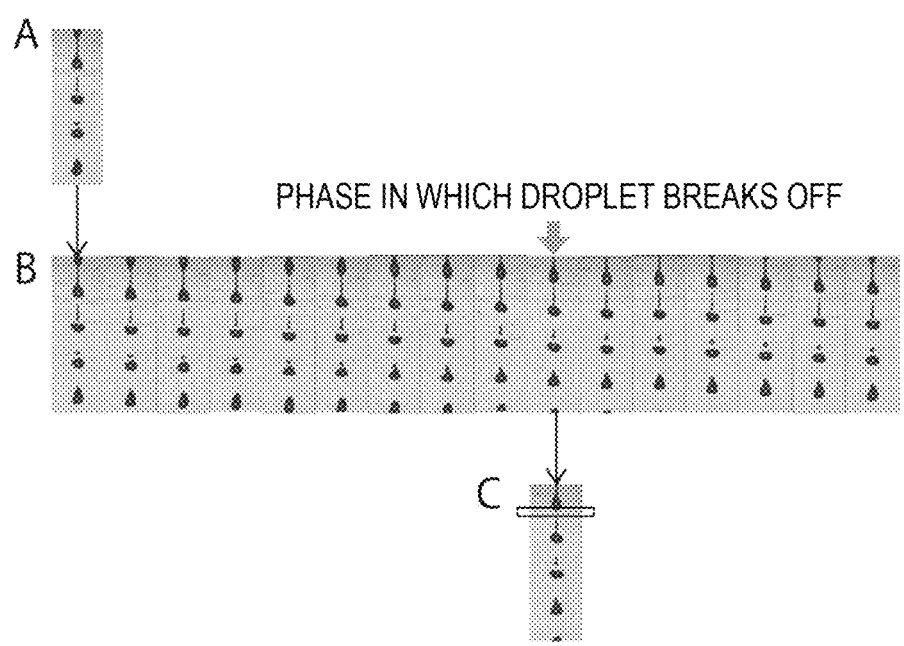
FIG. 7 A to C are diagrams illustrating a method of control example 2.

In the present control example 2, first, a droplet that is not spattering is created by automatically adjusting a droplet containing microparticles (see A of FIG. 7), as in control example 1. Then, a sequential photo with phases of a certain period is acquired while shaking the strobe, and phases in which a droplet breaks off (phases of timings at which a droplet breaks off) are specified (see B of FIG. 7) in the sequential photo. Although a phase of break-off is not as exactly specified as in the above-described control example 1 in this specification, control can be performed similarly to control example 1 as long as a distance of a gap generated from break-off is sufficiently short.

Then, a distances (gap) between a break-off point of the specified phase in which a droplet breaks off and a satellite is measured by monitoring the distance of the gap generated from the break-off, and the voltage of the vibration element 13 is adjusted so that a state in which break-off occurs in the same phase and the gap length is uniform can be maintained. If the gap increases, a droplet tends to break off, and thus the voltage of the vibration element 13 is lowered to reduce the gap. On the other hand, if the gap decreases, droplets tend to stick together, and thus the voltage of the vibration element 13 is increased to make it easy for a droplet to break off.

Control Example 3

Figure 8:
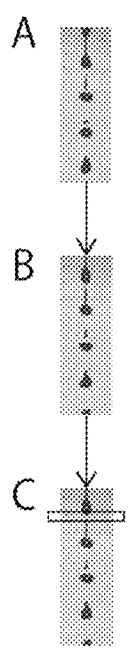
FIG. 8 A to C are diagrams illustrating a method of control example 3.

Control example 3 is a control example of a case in which a fast satellite occurs. In the present control example 3, first, a droplet containing microparticles is created (at this point, the droplet may be in a spattering state) (see A of FIG. 8). Then, a voltage of the vibration element 13 is adjusted so that a phase of a timing at which a droplet breaks off becomes a phase corresponding to the back azimuth of a phase in which electric charge is applied to microparticles in a certain period (see B of FIG. 8).

In the case in which a fast satellite occurs, spatter occurs if the order of break-off of a previous droplet, starting of application of electric charge, cutting of a target droplet, and ending of application of electric charge is not kept. Thus, the timing at which the previous droplet breaks off may be fixed to a phase before electric charge is applied. That is, since a droplet breaks off from a liquid column and then is separated as a satellite, it is better to pay attention only to the break-off of the droplet, and control can be performed using this method. For a specific droplet control method, the method in the control example 1 or control example 2 described above can be employed.

Note that, in the present control example 3, a plurality of photos of phases of certain times may be acquired by shaking the strobe before a voltage of the vibration element 13 is controlled.

Control Example 4

Figure 9:
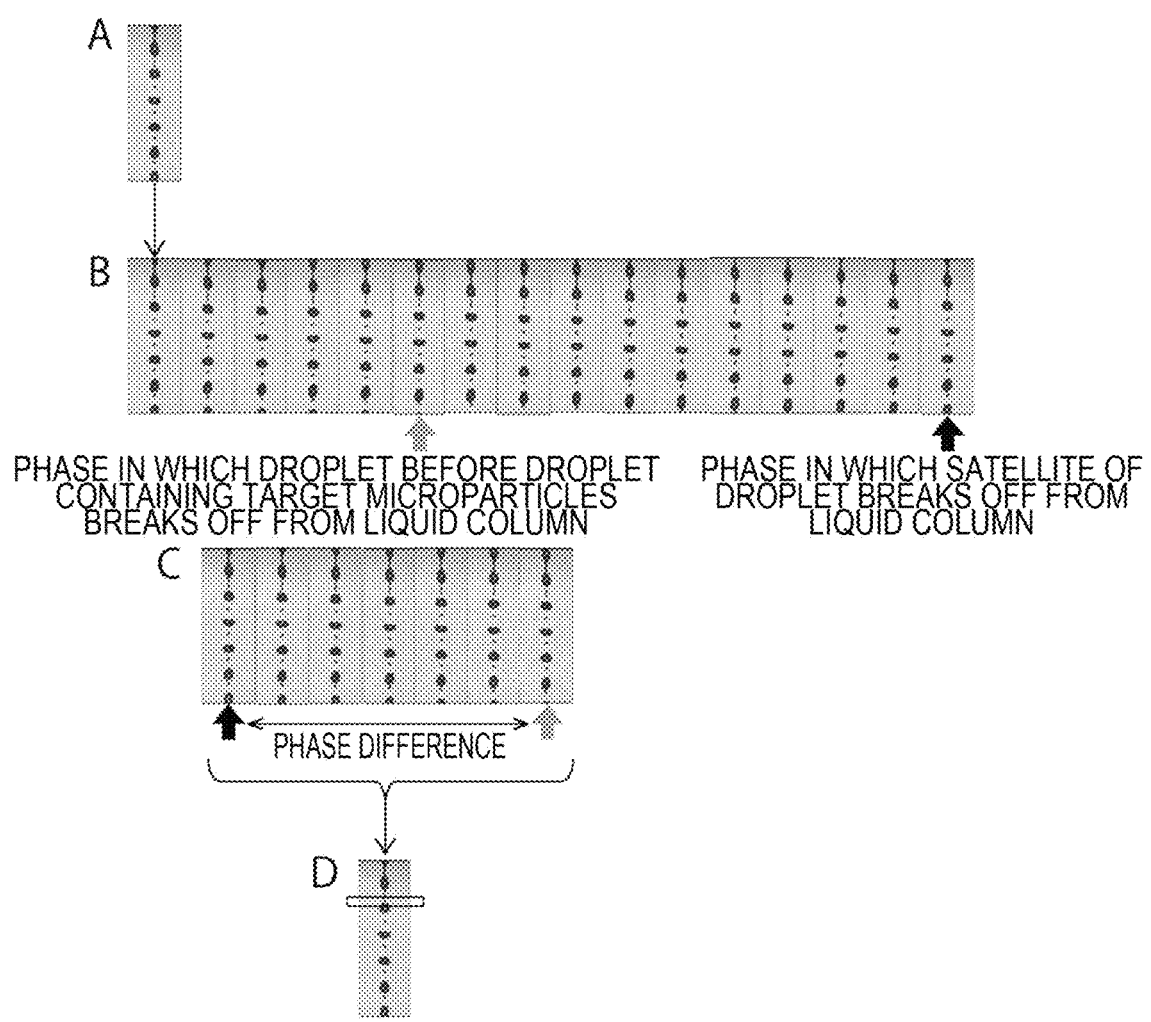
FIG. 9 A to D are diagrams illustrating a method of control example 4.

The control example 4 is a control example of a case in which a slow satellite occurs. In the present control example 4, first, a droplet containing microparticles is created (at this point, the droplet may be in a spattering state) (see A of FIG. 9). Then, a plurality of photos of phases of certain times are acquired while shaking the strobe, then a way of cutting a satellite of the droplet is examined, and then a phase in which the droplet before the droplet (a droplet containing target microparticles) breaks off from a liquid column and a phase in which the satellite of the droplet break off from the liquid column are specified (see B and C of FIG. 9). Then, a difference in the phases in which the satellite breaks off is examined, and then a voltage of the vibration element 13 is adjusted so that, for example, a phase in which electric charge is applied comes at the center.

In the case in which a slow satellite occurs, spatter occurs if an order of break-off of the droplet before the droplet containing the target microparticles from a liquid column, starting of application of electric charge, break-off of the satellite of the droplet from a liquid column, break-off of the droplet from the liquid column, and ending of application of electric charge is not kept. Since only one time of break-off from the liquid column occurs in the case of control example 3 (fast satellite), the voltage of the vibration element 13 may be adjusted so that the phase in which the droplet breaks off becomes a phase corresponding to the back azimuth of the phase in which electric charge is applied to the microparticles in one period, however, in the case of the slow satellite, if the phase matches the phase of the back azimuth, a wrong order of break-off of the droplet before the droplet containing the target microparticles from a liquid column, break-off of the satellite of the droplet from the liquid column, and starting of application of electric charge is set, and therefore, spatter occurs. Thus, in order to avoid the wrong order, it is necessary to specify the phase in which the droplet before the droplet (droplet containing target microparticles) breaks off from the liquid column and the phase in which the satellite of the droplet breaks off from the liquid column, measure a difference in the phases in which the satellite breaks off while shaking the strobe, or the like, and adjust the phase in which electric charge is applied to come at the center. For a specific droplet control method, the method in the control example 1 or control example 2 described above can be employed.

Note that, in the present technology, the control unit 4 may be configured to be able to control each unit of the microparticle analysis device 1 according to the present technology. In addition, the control unit 4 may be connected to each unit via a network.

(6) Detection Unit 5

The reference numeral 5 in FIG. 1 represents the detection unit 5 that detects measurement target light generated from microparticles such as cells or the like due to irradiation with a laser L1 emitted from a light source 51. The detection unit 5 detects microparticles included in a fluid circulating the flow path. The detection unit 5 detects characteristics of cells between the narrowing parts 261 and 262 of the sample flow path 22. The detection of characteristics is not particularly limited, and in a case of optical detection, for example, the detection unit 5 detects scattered light or fluorescence generated from cells by irradiating the cells being arrayed in one row and flowing at the center of the three-dimensional laminar flow on the sample flow path 22 with the laser L1 (see FIG. 1).

For the light irradiation and detection, an irradiation system such as a concentration lens, a dichroic mirror, or a band pass filter for collecting light and irradiating cells with laser may also be configured in addition to the laser light source. The detection system may be constituted by an area image sensor, for example, a photomultiplier tube (PMT), a CCD, or a CMOS element, and the like.

Measurement target light detected by the detection system of the detection unit 5 is light generated from the cells with irradiation with measurement light. Specifically, for example, the light is forward scattered light, side scattered light, scattered light of Rayleigh scattering or Mie scattering, or the like. The measurement target light is converted into electric signals, output to the above-described control unit 4, and provided for determination of optical characteristic of cells.

Note that the detection unit 5 may detect characteristics of cells magnetically or electrically. In this case, microelectrodes are arranged to face each other on the sample flow path 22 of the microchip 2, and a resistance value, a capacitance value (capacitance value), an inductance value, impedance, a changed value of electric fields of the electrodes, magnetization, a change in magnetic fields, a change in magnetizing fields, or the like can be measured.

(7) Deflecting Plates 61 and 62

The reference numerals 61 and 62 in FIG. 1 represent a pair of deflecting plates disposed to face each other sandwiching a droplet injected from the orifice 21 and captured by the imaging unit 3. The deflecting plates 61 and 62 are configured to include electrodes that control a movement direction of the droplet discharged from the orifice 21 using electric force acting on electric charge applied to the droplet. In addition, the deflecting plates 61 and 62 also control a trajectory of the droplet generated from the orifice 21 using electric force acting on electric charges applied to the droplet. In FIG. 1, the direction in which the deflecting plates 61 and 62 face each other is indicated as an X axis direction.

(8) Collection Containers 71 to 73

In the microparticle analysis device 1 according to the present technology, a droplet is accepted to any of the plurality of collection containers 71 to 73 arranged in a row in the direction (X axis direction) in which the deflecting plates 61 and 62 face each other. The collection containers 71 to 73 may be general-purpose plastic tubes or glass tubes for experiments. Although the number of collection containers 71 to 73 is not particularly limited, a case in which three collection containers are installed is illustrated here. Droplets generated from the orifice 21 are guided and collected to any one of the three collection containers 71 to 73 depending on the presence/absence or magnitude of electric force acting between the deflecting plates 61 and 62.

The collection containers 71 to 73 may be installed to be replaced with containers for collection containers (not illustrated). The containers for collection containers are arranged on, for example, a Z axis stage (not illustrated) configured to be movable in the direction (Z axis direction) orthogonal to the discharge direction (Y axis direction) of a droplet from the orifice 21 and the direction in which the deflecting plates 61 and 62 faces each other (X axis direction).

(9) Analysis Unit 8

The analysis unit 8 is connected to the detection unit 5 and analyzes detection values of light of microparticles detected by the detection unit 5.

The analysis unit 8 can, for example, correct a detection value of light received by the detection unit 5 and calculate feature amounts of each of microparticles. Specifically, feature amounts indicating sizes, shapes, internal structures, and the like of microparticles are calculated using detection values of received fluorescence, forward scattered light, and backward scattered light. In addition, sorting is determined on the basis of the calculated feature amounts, a sorting condition received by the input unit* beforehand, and the like, and thus a sorting control signal can be generated.

The analysis unit 8 is not essential for the particle analysis device 1 according to the present technology, and states of microparticles and the like can also be analyzed using an external analysis device or the like on the basis of a detection value of light detected by the detection unit 5. In addition, the analysis unit 8 may be connected to each unit via a network.

(10) Storage Unit 9

The storage unit 9 stores various items related to measurement including detection values of the detection unit 5, feature amounts calculated by the analysis unit 8, sorting control signals, sorting conditions input by the input unit, and the like.

The storage unit 9 is not essential for the microparticle analysis device 1, and an external storage device may be connected thereto. As the storage unit 9, for example, a hard disk or the like can be used. In addition, the recording unit 9 may be connected to each unit via a network.

(11) Display Unit 10

The display unit 10 can display all items related to analysis including detection values of the detection unit 5, and the like. Preferably, the display unit 10 can display feature amounts of each of microparticles calculated by the analysis unit 8 as a scattergram.

The display unit 10 is not essential for the microparticle analysis device 1 according to the present technology, and an external display device may be connected thereto. As the display unit 10, for example, a display, a printer, or the like can be used.

(12) Input Unit

The input unit (not illustrated) is a part operated by a user such as an operator. A user accesses the control unit 3 through the input unit, and thus can control each unit of the microparticle analysis device 1 according to the present technology. Preferably, the input unit can set a region of interest in a scattergram displayed on the display unit 10 and determine a sorting condition.

The input unit is not essential for the microparticle analysis device 1 according to the present technology, and an external operation device may be connected thereto. As the input unit, for example, a mouse, a keyboard, or the like can be used.

(13) Others

Note that, in the present technology, functions performed by each unit of the microparticle analysis device 1 according to the present technology can be stored in a personal computer or hardware resources with a control unit including a CPU or the like, a recording medium (e.g., a non-volatile memory (e.g., a USB memory, etc.), an HDD, a CD, etc.), and the like as programs, and can be caused to be exhibited by the personal computer or the control unit.

2. Microparticle Analysis Method

In a microparticle analysis method according to the present technology, at least a droplet formation step, an electric charge application step, an imaging step, and a control step are performed. In addition, another step may be performed if necessary. Each of the steps will be described below in detail.

(1) Droplet Formation Step

In the droplet formation step, by imparting vibration to a fluid composed of a sample flow containing microparticles and a sheath flow flowing to contain the sample flow using the vibration element, a droplet is formed in the fluid. Since a specific method used in the droplet formation step is similar to the method performed by the above-described droplet formation unit, description thereof is omitted here.

(2) Electric Charge Application Step

In the electric charge application step, electric charge is applied to a liquid containing the microparticles. Since a specific method used in the electric charge application step is similar to the method performed by the above-described electric charge application unit 11, description thereof is omitted here.

(3) Imaging Step

In the imaging step, photos of a phase of a certain time are obtained. Since a specific method used in the imaging step is similar to the method performed by the above-described imaging unit 3, description thereof is omitted here.

(4) Control Step

Since a specific method used in the control step is similar to the method performed by the above-described control unit 4, description thereof is omitted here.

Note that it is preferable in the control step to adjust a voltage of the vibration element 13 on the basis of a timing at which a droplet specified in the plurality of photos breaks off.

[One Example of Analysis Flow of Microparticles]

Figure 10:
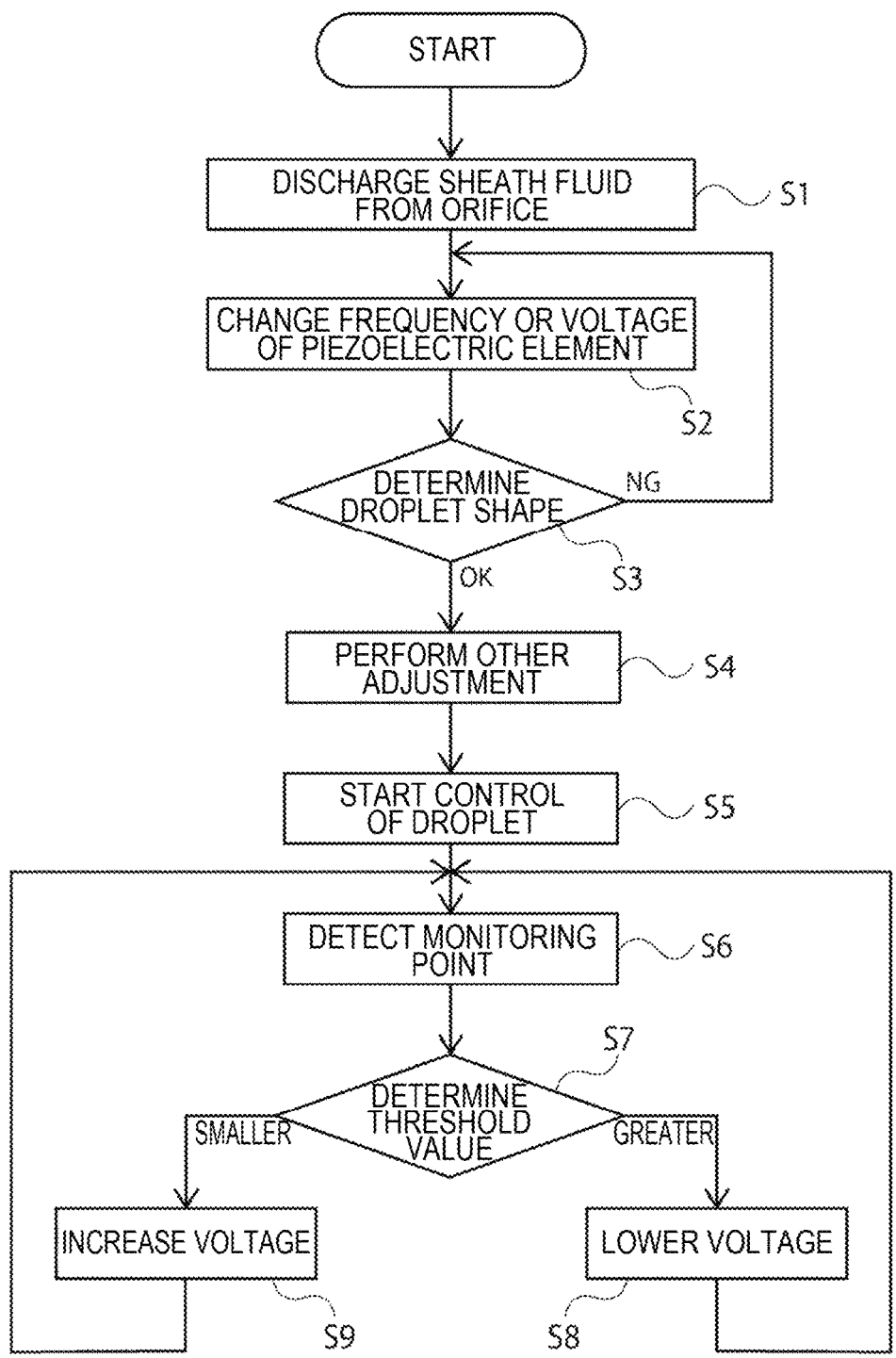
FIG. 10 is a flowchart showing an example of a flow of microparticle analysis using the microparticle analysis method according to the present technology.

An example of an analysis flow of microparticles using the microparticle analysis method according to the present technology will be described with reference to FIG. 10. Note that a process of each step of the flowchart illustrated in FIG. 10 is performed by, for example, each of the above-described units.

First, a sheath fluid is discharged from the orifice 21 of the microchip 2 (Step S1). Then, the control unit 4 changes a frequency or a voltage of a piezoelectric element serving as the vibration element 13 (Step S2). Then, the control unit 4 determines a droplet shape (Step S3). If the droplet shape is defective, the process returns to Step S2. If the droplet shape is favorable, other adjustment is performed (Step S4). Specifically, although adjustment of finding a break-off point shaking the strobe is performed in Step S4, this step is not necessary in the microparticle analysis method according to the present technology. Steps S1 to S4 are steps in which automatic adjustment of a droplet is performed, and by performing the steps, a condition of the droplet appropriate for sorting (e.g., a length and a position of the droplet, a direction in which a satellite is absorbed (fast or slow), etc.) is set advance for the device, a frequency or a voltage of the vibration element 13 is changed, and thereby a droplet satisfying the target condition is searched for.

After Step S4, the control unit 4 starts control of a droplet (Step S5). First, the control unit 4 detects a monitoring point (Step S6). The monitoring point is a moment at which a droplet containing microparticles breaks off in a phase of a certain time. To aim the monitoring point, the methods described in the above-described control examples 1 to 4, and the like are exemplified. A threshold value set for the monitoring point is determined (Step S7), and if the value of the monitoring point is greater than the threshold value, the voltage of the vibration element 13 is lowered (Step S8). On the other hand, if the value of the monitoring point is smaller than the threshold value, the voltage of the vibration element 13 is increased (Step S9). Steps S4 to S9 are steps in which control of a droplet is performed, and by performing the steps, the moment in which a droplet breaks off from a liquid column can be continuously monitored, the break-off timing can be constantly retained by directly maintaining the state, and thus stable sorting can be realized.

Additionally, the present technology may also be configured as below.

(1)

A microparticle analysis device including at least:

a flow path in which a fluid including a sample flow containing microparticles and a sheath flow flowing to contain the sample flow;

a droplet formation unit configured to form a droplet in the fluid by imparting vibration to the fluid using a vibration element;

an electric charge application unit configured to apply electric charge to a droplet containing the microparticles;

an imaging unit configured to obtain a photo of a phase of a certain time; and a control unit configured to control a timing at which the droplet breaks off on a basis of the photo.

(2)

The microparticle analysis device according to (1), in which the control unit adjusts a voltage of the vibration element on a basis of a timing at which the droplet specified in a plurality of the photos breaks off.

(3)

The microparticle analysis device according to (1) or (2), in which the control unit acquires a sequential photo of a phase of one period and specifies a phase of a timing at which the droplet breaks off in the sequential photo.

(4)

The microparticle analysis device according to (3), in which the control unit acquires a sequential photo in which phases before and after the phase of the timing at which the droplet breaks off are further divided, and specifies a phase of a timing at which the droplet breaks off in the divided sequential photo.

(5)

The microparticle analysis device according to (3) or (4), in which the imaging unit includes a strobe, and the specification is performed using a sequential phase photo obtained by changing a strobe light emission start time of the strobe.

(6)

The microparticle analysis device according to any of (1) to (5), in which the control unit performs control such that a phase of a timing at which the droplet breaks off becomes a phase corresponding to a back azimuth of a phase in which electric charge is applied to the droplet.

(7)

The microparticle analysis device according to any of (1) to (6), in which the control unit performs control such that a phase in which electric charge is applied to the droplet comes between a phase in which a droplet before the droplet breaks off from a liquid column and a phase in which a satellite of the droplet breaks off from a liquid column.

(8)

A microparticle analysis method including at least:

a droplet formation step of forming a droplet in a fluid including a sample flow containing microparticles and a sheath flow flowing to contain the sample flow by imparting vibration to the fluid using a vibration element;

an electric charge application step of applying electric charge to a droplet containing the microparticles;

an imaging step of obtaining a photo of a phase of a certain time; and a control step of controlling a timing at which the droplet breaks off on a basis of the photo.

(9)

The microparticle analysis method according to (8), in which, in the control step, a voltage of the vibration element is adjusted on a basis of a timing at which the droplet specified in a plurality of the photos breaks off.

REFERENCE SIGNS LIST 1 microparticle analysis device
11 electric charge application unit
12 electrode
13 vibration element
2 microchip
2a, 2b substrate layer
21 orifice
22 sample flow path
23 sample inlet
24 sheath inlet
25 suction flow path
27 straight part
211 notch
251 suction outlet
252 communication port
261, 262 narrowing part
3 imaging unit
31 strobe
32 droplet camera
4 control unit
5 detection unit
51 light source
61, 62 deflecting plate
71 to 73 collection container
8 analysis unit
9 storage unit
10 display unit

The invention claimed is:

1. A microparticle analysis device comprising:
a microchip defining a flow path in which a fluid includes a sample flow containing microparticles and a sheath flow to contain the sample flow;
a vibration element configured to form a droplet in the fluid by imparting vibration to the fluid;
an electrode configured to apply electric charge to a droplet containing the microparticles;
an imaging unit configured to acquire a plurality of sequential images of the sample flow during a predetermined period; and
a control unit configured to control a timing at which the droplet breaks off the sample flow on a basis of the plurality of sequential images of the sample flow, the control unit including a processor and a memory containing instructions that, when executed by the processor, are configured to:
determine a phase of the predetermined period at which the droplet breaks off the sample flow based on the plurality of sequential images;
determine a break-off position of the droplet in an image of the plurality of sequential images at the determined phase of the predetermined period at which the droplet breaks off the sample flow; and
adjust a voltage of the vibration element based on the determined break-off position of the droplet.

2. The microparticle analysis device according to claim 1, wherein the control unit is configured to acquire additional images in which phases before and after the phase of the predetermined period at which the droplet breaks off the sample flow are further divided, and to determine a phase of the sample period at which the droplet breaks off in the additional images.

3. The microparticle analysis device according to claim 1, further including a strobe, wherein the determination of the phase is performed using a the plurality of sequential images obtained by changing a strobe light emission start time of the strobe.

4. The microparticle analysis device according to claim 1, wherein the control unit performs control such that the phase in which the droplet breaks off the sample flow is a phase corresponding to a back azimuth of a phase in which electric charge is applied to the droplet.

5. The microparticle analysis device according to claim 1, wherein the control unit performs control such that a phase in which electric charge is applied to the droplet comes between a phase in which a droplet before the droplet breaks off from the sample flow and a phase in which a satellite of the droplet breaks off from the sample flow.

6. A microparticle analysis method comprising:
forming a droplet in a fluid including a sample flow containing microparticles and a sheath flow to contain the sample flow by imparting vibration to the fluid using a vibration element;
applying electric charge to a droplet containing the microparticles;
acquiring a plurality of sequential images of the sample flow during a predetermined period; and
controlling a timing at which the droplet breaks off the sample flow on a basis of the plurality of images of the sample flow, wherein controlling comprises:
  determining a phase of the predetermined period at which the droplet breaks off the sample flow based on the plurality of sequential images;
  determining a break-off position of the droplet in an image of the plurality of sequential images at the determined phase of the predetermined period at which the droplet breaks off the sample flow; and
  adjusting a voltage of the vibration element based on the determined break-off position of the droplet.

\* \* \* \* \*